United States Patent [19]

Yamamoto et al.

[11] Patent Number: 4,959,220

[45] Date of Patent: Sep. 25, 1990

[54] ANTISEPTIC-CONTAINING ALGINATE IMPRESSION MATERIAL

[75] Inventors: Tameyuki Yamamoto, Kamakura; Masao Abiru, Omiya, both of Japan

[73] Assignee: G-C Dental Industrial Corporation, Tokyo, Japan

[21] Appl. No.: 256,566

[22] Filed: Oct. 12, 1988

[30] Foreign Application Priority Data

Oct. 12, 1987 [JP] Japan .................................. 62-254623

[51] Int. Cl.⁵ ................................................ A61K 9/16
[52] U.S. Cl. ..................................... 424/490; 424/490; 424/497
[58] Field of Search ........................ 424/490, 497, 495; 264/4, 6

[56] References Cited

U.S. PATENT DOCUMENTS

| | | | |
|---|---|---|---|
| 4,702,904 | 10/1987 | Maeyama et al. | 424/49 |
| 4,711,782 | 12/1987 | Okada et al. | 424/497 |
| 4,725,657 | 2/1988 | Shibanai | 424/78 |
| 4,836,853 | 6/1989 | Gribi | 106/205 |

*Primary Examiner*—Merrell C. Cashion, Jr.
*Assistant Examiner*—P. L. Prater
*Attorney, Agent, or Firm*—Oblon, Spivak, McClelland, Maier & Neustadt

[57] ABSTRACT

An antiseptic-containing alginate impression material contains 0.01 to 7 parts by weight of an antiseptic such as glutaraldehyde and chlorohexydine gluconate per 100 parts by weight of a cured product of an alginate impression material. The antiseptic may be encapsulated in a microcapsule or clathrated in a cyclodextrin.

16 Claims, No Drawings

ANTISEPTIC-CONTAINING ALGINATE IMPRESSION MATERIAL

BACKGROUND OF THE INVENTION

1. Field of the Invention

The present invention has for its object to prevent the contagion of infectious diseases during dental impression-taking, and relates to an antiseptic-containing alginate impression material intended to eliminate the contagion of infectious diseases from counter-dies of impression materials by previously incorporating a specific amount of an antiseptic innoxious to the human body into the powders of alginate impression materials.

2. Statement of the Prior Art

During dental examination and treatment, dentists or dental technicians may often catch pathogenic bacteria or viruses via the blood or sputum of a patient suffering from an infectious disease. For that reason, they wear protecting gloves, masks, caps and glasses during dental examination and treatment, thereby preventing a direct contact of the patient's blood or sputum with them. It is also common sense with them to sterilize dental instruments contaminated with the blood or sputum of a patient suffering from an infectious disease by the application of heat or chemicals.

For a patient suffering from an infectious disease, a handpiece in place of a turbine is used to prevent splattering of cuttings, blood or sputum, and an antiseptic is discharged to a vacuum arrangement and a discharge system so as to attempt preventing contamination.

Although it is preventable for dentists, dental technicians or other patients to catch direct infection from infectious diseases, as mentioned above, yet pathogenic bacteria or viruses carried by blood or sputum remain deposited onto the counter-die of an impression material taken out of the mouth of an infected patient. When gypsum is cast in the counter-die of the impression material, onto which pathogenic bacteria or viruses remain deposited, in making a gypsum model, such bacteria or viruses are carried onto the surface of the gypsum model. Thus, dental technicians manipulate the gypsum model infected by pathogenic bacteria or viruses, touching them all the while.

This further leads to a fear that such pathogenic bacteria or viruses may be carried in the body system through a wound in the hand or foodstuffs taken in by way of an infected hand. It is understood that with a view to preventing the contagion of an infectious disease through such an impression material, the counter-dies thereof are usually disinfected by chemicals, as mentioned just below.

The counter-die of an impression material is first well washed with water, and is then immersed in an about 1 to 5% aqueous solution of sodium hypochlorite for about 10 to 30 minutes. Since sodium hypochlorite is a very unstable substance, however, such solutions should all be prepared every day and done away with after use.

In some cases, use may be made of formaldehyde. After washing with water, a counter-die is dipped in an about 3 to 8% aqueous solution of formaldehyde or an 8% solution of formaldehyde in 70% of an alcohol for about 10 to 30 minutes. Still alternatively, the counter-die of an impression material may be dipped in an aqueous solution of glutaraldehyde or an iodine compound for about 10 to 30 minutes. Still alternatively, the counter-die of an impression material may be sprayed with an about 1 to 5% aqueous solution of sodium hypochlorite or an about 1 to 5% aqueous solution of an iodine compound by means of spray equipment filled therewith.

With regard to the methods involving immersion of the counter-die of an impression material having pathogenic bacteria or viruses deposited thereonto in an antiseptic solution for about 10 to 30 minutes for the purpose of killing off such bacteria or viruses, there are some disadvantages, as stated below.

(1) The operation of disinfecting the counter-die of an impression material by immersing it in an antiseptic solution tends to slip from memory or be omitted through inadvertence, since it is not included in the essential steps of preparing a gypsum model by casting gypsum on the counter-die.

(2) Since the operation of immersing the counter-die of an impression material in an antiseptic solution for about 10 to 30 minutes is reluctant to carry out, a general tendency is that the counter-die of an impression material is only washed with water, while its immersion in an antiseptic solution is left undone. Thus, it is now still impossible to completely prevent the contagion of an infectious disease.

To spray the counter-die of an impression material with an antiseptic solution by means of spray equipment filled therewith is a simple procedure, but has the following demerits.

(1) The operation for spraying the counter-die of an impression material with an antiseptic solution by means of spray equipment filled therewith is prone to slip from memory, since it is not included in the essential steps of preparing a gypsum model by casting gypsum on that counter-die.

(2) Spraying of an antiseptic solution does not assure any sufficient disinfecting effect, since the counter-die of an impression material is only washed with water with the lapse of a short time after it has been sprayed with an antiseptic solution by means of spray equipment filled therewith.

(3) It is difficult to achieve effective disinfection, since an antiseptic solution is neither evenly sprayed over the entire surface of the counter-die of an impression material nor sufficiently sprayed on an undercut portion, etc.

SUMMARY OF THE INVENTION

The present invention relates to the disinfection of a counter-die of an impression material, and provides a novel antiseptic-containing alginate impression material comprising an alginate impression material and containing a powdered antiseptic which is not noxious the human body which is dispersed in a required amount throughout said impression material, which is adapted to expel the antiseptic from the alginate impression material at the time of kneading with water simultaneously with disinfecting the counter-die of said impression material.

DETAILED DESCRIPTION OF THE INVENTION

The antiseptic-containing alginate impression materials according to the present invention will now be explained in detail. According to the antiseptic-containing alginate impression materials of the present invention, the amount of antiseptics used is in a range of 0.01 to 7 parts by weight per 100 parts by weight of a cured product of alginate impression materials. Preference is given to 0.5 to 5 parts by weight. In the present disclosure, by the "cured product" of alginate impression materials is meant a product obtained just after 16 parts by weight of alginate impression material powders have been mixed and cured with 40 parts by weight of water. Various antiseptics may be used to this end and, by way of example alone, include phenol, p-chlorophenol, bithionol, chlorohexydine, iodoform, iodinated phenol, trichloroisocyanuric acid, calcium hypochlorite, sodium hypochlorite, a mercury compound, benzalconiumchloride, glutaraldehyde, aqueous hydrogen peroxide, chlorohexydine gluconate, povidone iodine, benzalconium chloride, benzethonium chloride and ethanol. Preference is given to glutaraldehyde, sodium hypochlorite, aqueous hydrogen peroxide, chlorohexadine gluconate, povidone iodine and benzalconium chloride. Glutaraldehyde is effective for bacteria and viruses; sodium hypochlorite, for bacteria, viruses and other microbes; aqueous hydrogen peroxide, for anaerobic bacteria, gram-positive bacteria and fungi; povidone iodine, for bacterial, viruses and fungi; benzalconium chloride, for gram-positive and negative bacteria; and benzethonium chloride, for fungi. For such reasons, they have been utilized as antiseptices for long years on account of their well-accepted antiseptic effects.

Such antiseptics may be dispersed throughout alginate impression material powders by various methods. The antiseptic may be dispersed directly throughout alginate impression material powders. With the storage stability of antiseptics in mind, however, better results are obtained if they are encapsulated in microcapsules, dispersed throughout less reactive powders, followed by surface-treating with a hydrophobic liquid or clathrated in a cyclodextrin. Referring first to the method for encapsulating an antiseptic in microcapsules, when a water-soluble antiseptic is used with microcapsules, it is required that a substance forming the shells of microcapsules is lipophilic. The lipophilic substances used may include thermoplastic substances such as polyethylene, polypropylene and polyurethane; hydrocarbons such as paraffin wax and microcrystalline wax; waxes such as beeswax, synthetic spermaceti, Japan wax and carnauba wax; and higher alcohols such as palmitic acid, stearic acid and serotinic acid. For the preparation of antiseptic-containing microcapsules, generally, the antiseptic to be encapsulated in microcapsules is dissolved in water to prepare an aqueous solution, which is then dispersed in a melt obtained by heating the substance forming the shells of microcapsules, followed by cooling, according to conventional manners.

In another embodiment of the present invention, the antiseptic is adsorbed onto powders poor in reactivity, which are then treated on their surfaces with a hydrophobic liquid and dispersed throughout the powders of an alginate impression material. More specifically, the powders poor in reactivity refer to those of diatomaceous earth, talc and quartz, and are mixed with the antiseptic to be adsorbed thereonto. Thereafter, they are mixed with a hydrophobic liquid (oils and fats, fatty acid esters, liquid paraffin, etc.) to coat their surfaces with a hydrophobic liquid, and are then disperesed throughout the powders of an alginate impression material.

In a further embodiment of the present invention, the antiseptic is clathrated in a cyclodextrin. The cyclodextrin is obtained by the action of a special transferase, i.e., cyclodextrin glucanotransferase upon starch, and assumes a special structure of 6 to 12 glucoses bonded together in a form of a ring. Basically, three types of cyclodextrins, $\alpha$-cyclodextrin, $\beta$-cyclodextrin and $\gamma$-cyclodextrin are available, and are mixed together or processed for use. The cyclodextrin is mixed with water to prepare a saturated aqueous solution, in and with which the antiseptic is added and mixed to form precipitates in which the antiseptic is clathrated in the cyclodextrin. Then, the water content of the precipitates is evaporated off to prepare powders containing the antiseptic in the cyclodextrin, which are to be dispersed throughout the powders of an alginate impression material.

By the methods as mentioned above, a suitable amount of the antiseptic is dispersed throughout an alginate impression material. At the time when the antiseptic-containing alginate impression material is kneaded with water, the antiseptic contained in the microcapsules, etc. is physically expelled therefrom by direct dissolution in water or spatulation for simple and flawless disinfection of the counter-die of the alginate impression material itself. It is thus possible to entirely eliminate conventional troublesome work for disinfection, incomplete disinfection or a possibility of disinfection work slipping from memory.

EXAMPLES

The present invention will now be explained specifically but not exclusively with reference to the following examples.

EXAMPLE 1

|  | pbw |
| --- | --- |
| Sodium Alginate | 15 |
| Calcium Sulfate Dihydrate | 15 |
| Trisodium Phosphate | 2 |
| Diatomaceous Earth | 60 |
| Talc | 5 |
| Titanium Potassium Fluoride | 1 |
| Aluminum Oxide | 2 |
| Microcapsules in which a sodium hypochlorite solution (with the concentration being 20% by weight) was coated with a thin polyurethane film) | 0.5 |

All the components in the above but the microcapsules were blended together in a blender with the dropwise addition of 8 parts by weight of squalane. Thereafter, the microcapsules were uniformly mixed with the blend with much care to prepare the antiseptic-containing alginate impression material powders according to the present invention. Sixteen (16) parts by weight of the obtained powders and 40 parts by weight of water were kneaded together in a rubber bowl by means of a spatula in the conventional manners.

EXAMPLE 2

Similar components as used in Ex. 1 were employed, except for the microcapsules in which a sodium hypochlorite solution (having a concentration of 20% by weight) was coated with a thin polyurethane film and diatomaceous earth. Two (2) parts by weight of chlorohexydine gluconate and 10 parts by weight of liquid paraffin were first mixed with 60 parts by weight of diatomaceous earth to treat the surface of chlorohexydine gluconate having diatomaceous earth adsorbed thereonto with liquid paraffin.

Seventy-two (72) parts by weight of the resulting product were added to and blended with all the components of example 1 (but diatomaceous earth and the capsules) in a blender with the dropwise addition of 8 parts by weight of squalane. Sixteen (16) parts by weight of the obtained powders and 40 parts by weight of water were kneaded together in a rubber bowl by means of a spatula according to the conventional manners.

EXAMPLE 3

Similar components as used in Ex. 1 were used, except for the microcapsules in which a sodium hypochlorite solution (having a concentration of 20% by weight) was coated with a thin polyurethane film. Fifty (50) parts by weight of glutaraldehyde were added to a solution of 150 parts by weight of ISOELEAT·L (a trade name of cyclodextrin manufactured by Nikken Kagaku, K. K.) for about one-hour agitation. The resulting precipitates were dried to prepare powders of ISOELEAT·L having glutaraldehyde clathrated therein. The components used in Ex. 1 except for the capsules were added to and blended with 4 parts by weight of the obtained powders in a blender with the dropwise addition of 8 parts by weight of squalane. Sixteen (16) parts by weight of the obtained powders and 40 parts by weight of water were kneaded together in a rubber bowl by means of a spatula according to the conventional manner.

EXAMPLE 4

Forty (40) parts by weight of water and 16 parts by weight of powders of VERICOL AROMA DUST FREE (a tradename of the alginate impression material manufactured by G-C Dental Industrial Corp.) were kneaded with 0.57 parts by weight of glutaraldehyde in a rubber bowl by means of a spatula according to the conventional manner.

EXAMPLE 5

Example 4 was repeated, except that 0.3 parts by weight of glutaraldehyde were used.

EXAMPLE 6

Example 4 was repeated, except that 2.85 parts by weight of glutaraldehyde were used.

EXAMPLE 7

Forty (40) parts by weight of water and 16 parts by weight of powders of VERICOL AROMA DUST FREE (a tradename of the alginate impression material manufactured by G-C Dental Industrial Corp.) were kneaded with 0.57 parts by weight of chlorohexydine gluconate in a rubber bowl by means of a spatula according to the conventional manner.

EXAMPLE 8

Example 7 was repeated, except that 0.3 parts by weight of chlorohexydine gluconate were used.

EXAMPLE 9

Example 7 was repeated, except that 2.85 parts by weight of chlorohexydine gluconate were used.

COMPARATIVE EXAMPLE 1

Example 1 was repeated, except that 5.7 parts by weight of glutaraldehyde were used.

COMPARATIVE EXAMPLE 2

Example 7 was repeated, except that 5.7 parts by weight of chlorohexydine gluconate were used.

STANDARD SAMPLE

Sixteen (16) parts by weight of powders of VERICOL AROMA DUST FREE (a tradename of the alginate impression material manufactured by G-C Dental Industrial Corp.) were kneaded with 40 parts by weight of water in a rubber bowl by means of a spatula according to conventional manners.

The physical data of the products of Examples 1 to 9 and Comparative Examples 1-2 as well as the standard sample are summarized in Table 1.

TABLE 1

| Example Comparative Example Standard Sample | <Based Upon JIS T6505> | | |
|---|---|---|---|
| | Curing Time (Minute) | Elastic Strain (%) | Permanent Strain (%) |
| Example 1 | 1.5 | 12.8 | 3.0 |
| Example 2 | 2 | 13.0 | 3.0 |
| Example 3 | 2 | 13.2 | 2.9 |
| Example 4 | 2 | 12.9 | 2.9 |
| Example 5 | 2 | 13.0 | 3.1 |
| Example 6 | 2 | 13.1 | 3.0 |
| Example 7 | 2 | 13.2 | 3.0 |
| Example 8 | 2 | 13.1 | 2.9 |
| Example 9 | 2.5 | 12.8 | 2.8 |
| Comparative Example 1 | Curing Poor | Measuring not Possible | Measuring not Possible |
| Comparative Example 2 | Curing Poor | Measuring not Possible | Measuring not Possible |
| Standard Sample | 2 | 13.2 | 2.9 |

In Example 1, the microcapsules, in which a sodium hypochlorite solution (having a concentration of 20% by weight) was coated with a thin polyurethane film, were dispersed throughout the alginate impression material powders. The microcapsules were sufficiently broken into pieces by a physical force produced when the dispersion was kneaded with water, thereby to expel an aqueous solution of sodium hypochlorite therefrom. Thus, the product of Ex. 1 is expected to have an effect upon entirely disinfecting the alginate impression material.

In Example 2, diatomaceous earth having chlorohexydine gluconate adsorbed thereonto was coated with a thin film of liquid paraffin, and was then mixed with other composition forming an alginate impression material. By kneading the resulting mixture with water, chlorohexydine gluconate was easily expelled therefrom. Thus, the product of Ex. 2 is expected to have an effect upon entire disinfecting of the alginate impression material.

In Example 3, glutaraldehyde clathrated in cyclodextrin was mixed with other composition forming an alginate impression material. When kneaded with water, glutaraldehyde was readily expelled out of the obtained mixture. Thus, the product of Ex. 3 is expected to have an effect upon entire disinfecting of the alginate impression material.

Examples 4 to 9 and Comparative Examples 1 to 2 were provided to determine an influence upon the physical properties which the contents of chlorohexydine gluconate and glutaraldehyde gave to the alginate impression materials. Examples 4 to 9 were found to be comparable to the standard sample. However, the products of Comparative Examples 1 and 2 were found to have an adverse influence upon the physical properties of the alginate impression materials and make it impossible to use them. Although varying with the type of antiseptics and the regions to be disinfected, the effect of the antiseptics per se is considered to be sufficiently assured in a content of 0.05 to 5% by weight.

It is noted that referring to chlorohexydine gluconate, there are generally available the following data, which would hold for gelated cured products as well.

| Efficacy or Curing | Use and Quantity | Example of Use |
|---|---|---|
| Disinfection of fingers, skin | 0.1~0.5% solution | Normal 0.1% solution (Over 30 seconds) Contaminated 0.5% solution (Over 30 seconds) |
| Disinfection of skin on the part subject to operation | 0.1~0.5% solution or 0.5% ethanol solution | 0.5% ethanol solution |
| Disinfection of skin on the part injured | 0.05% solution | 0.05% solution |
| Disinfection of medical treatment instruments | 0.1~0.5% solution or 0.5% ethanol solution | Normal 0.1% solution (10~30 minutes) Contaminated 0.5% solution (Over 30 minutes) Emergent 0.5% ethanol solution (Over 2 minutes) |
| Disinfection of operation room, sick ward, furniture, utensile, goods etc. | 0.05% solution | 0.05% solution |

It is thus possible to entirely eliminate the defects (1) and (2) inherent in the conventional method in which the counter-die of an impression material is immersed in an antiseptic solution for about 10 to 30 minutes so as to kill off pathogenic bacteria or viruses deposited thereonto.

(1) The operation of the counter-die of an impression material being disinfected by immersing it in an antiseptic solution tends to slip from memory or be omitted through inadvertence, since it is not included in the essential steps of preparing a gypsum model by casting gypsum on the counter-die.

(2) Since the operation of immersing the counter-die of an impression material in an antiseptic solution for about 10 to 30 minutes is reluctant to carry out, a general tendency is that the disinfection of such a counter-die is carried out only by washing with water, while its immersion in an anticeptic solution is omitted.

It is also possible to completely eliminate the demerits (1), (2) and (3) inherent in the method in which the counter-die of an impression material is sprayed with an antiseptic solution by means of spray equipment filled therewith.

(1) The operation of spraying the counter-die of an impression material with an antiseptic solution by means of spray equipment filled therewith is prone to slipping from memory or being omitted, since it is not included in the essential steps of preparing a gypsum model by casting gypsum on that counter-die.

(2) Spraying of an antiseptic solution does not assure any sufficient disinfecting effect, since the counter-die of an impression material is washed with water with the lapse of a short time after it has been sprayed with an antiseptic solution by means of spray equipment filled therewith.

(3) It is difficult to achieve effective disinfection, since an antiseptic solution is neither evenly sprayed over the entire surface of the counter-die of an impression material nor sufficiently sprayed on an undercut portion, etc.

Thus, the antiseptic-containing alginate impression materials according to the present invention assure elimination of the defects of the conventional methods. In some cases, the antiseptic may be dispersed in an aqueous component at the time of kneading of alginate impression material.

It is noted that a plurality of antiseptics may be mixed together for use. It is also noted that similar effects as in the present invention may be obtainable with gypsum materials, investing materials, epoxy model materials and boxing materials such as clay and wax containing the antiseptics used for the present invention.

Effect of the Invention

The object of the present invention is to prevent the contagion of infectious diseases, which tend to occur through the counter-die of an alginate impression material during dental examination and treatment. In order to achieve this object, the antiseptic is previously contained in the powders of an alginate impression material, while subjected to storage stabilization. When kneaded with water, the antiseptic is easily expelled from the antiseptic-containing alginate impression material, whereby such a counter-die can be simply and flawlessly disinfected as such. It is thus possible to completely eliminate a troublesome disinfecting operation, incomplete disinfection and a tendency for a disinfecting operation to slipping from memory which have all been encountered in the prior art, thus making a considerable contribution to dental examination and treatment.

What is claimed is:

1. An antiseptic-containing alginate impression material which contains 0.01 to 7 parts by weight of an antiseptic material per 100 parts by weight of cured product of dental alginate impression material, wherein said antiseptic material is either encapsulated in a microcapsule or clathrated in a cyclodextrin.

2. The antiseptic-containing alginate impression material of claim 1, wherein said antiseptic material is encapsulated in a microcapsule.

3. The antiseptic-containing alginate impression material of claim 2, wherein said antiseptic material is glutaraldehyde.

4. The antiseptic-containing alginate impression material of claim 2, wherein said antiseptic material is chlorohexydine gluconate.

5. The antiseptic-containing alginate impression material of claim 1, wherein said antiseptic material is clathrated.

6. The antiseptic-containing alginate impression material of claim 5, wherein said antiseptic material is glutaraldehyde.

7. The antiseptic-containing alginate impression material of claim 5, wherein said antiseptic material is chlorohexydine gluconate.

8. The antiseptic-containing alginate impression material of claim 2, containing 0.5 to 5 parts by weight of said antiseptic material.

9. The antiseptic-containing alginate impression material of claim 5, containing 0.5 to 5 parts by weight of said antiseptic material.

10. The antiseptic-containing alginate impression material of claim 1, wherein said antiseptic material is at least one member selected from the group consisting of phenol, p-chlorophenol, bithionol, chlorohexydine, iodoform, iodinated phenol, trichloroisocyanuric acid, calcium hypochlorite, sodium hypochlorite, antiseptic mercury compounds, benzalconiumchloride, glutaraldehyde, aqueous hydrogen peroxide, chlorohexydine gluconate, povidone iodine, benzalkonium chloride, benzethonium chloride and ethanol.

11. The antiseptic-containing alginate impression material of claim 1, wherein said antiseptic material is at least one member selected from the group consisting of glutaraldehyde, sodium hypochlorite, aqueous hydrogen peroxide, chlorohexadine gluconate, povidone iodine and benzalkonium chloride.

12. The antiseptic-containing alginate impression material of claim 1, wherein said microcapsule comprises, as a shell-forming substance, a thermoplastic substance, a hydrocarbon, a wax, or a higher alcohol.

13. The antiseptic-containing alginate impression material of claim 2, wherein said microcapsule comprises, as a shell-forming substance, polyethylene, polypropylene, polyurethane, paraffin wax, microcrystalline wax, bees wax, synthetic spermaceti, Japan wax, carnauba wax, palmitic acid, stearic acid or serotinic acid.

14. The antiseptic-containing alginate impression material of claim 5, wherein said cyclodextrin is an alphacyclodextrin.

15. The antiseptic-containing alginate impression material of claim 5, wherein said cyclodextrin is a betacyclodextrin.

16. The antiseptic-containing alginate impression material of claim 5, wherein said cyclodextrin is a gammacyclodextrin.

* * * * *